(12) United States Patent
Ikeuchi et al.

(10) Patent No.: US 7,179,285 B2
(45) Date of Patent: Feb. 20, 2007

(54) STENT

(75) Inventors: Takeshi Ikeuchi, c/o Kyoto University 53, Shogoin-Kawaharacho, Sakyo-ku, Kyoto-shi (JP) 606-8397; Kouji Mori, c/o Kyoto University 53, Shogoin-Kawaharacho, Sakyo-ku, Kyoto-shi (JP) 606-8397; Hiroo Iwata, c/o Kyoto University 53, Shogoin-Kawaharacho, Sakyo-ku, Kyoto-shi (JP) 606-8397; Kazuaki Mitsudou, 597-11, Fukushima, Kurashiki-shi, Okayama (JP) 710-0048; Hiroaki Nomiyama, Oita (JP); Yoshiharu Yoshikawa, Oita (JP); Masatoshi Watanabe, Oita (JP)

(73) Assignees: Kawasumi Laboratories, Inc., Tokyo (JP); Kazuaki Mitsudou, Kurashiki (JP); Takeshi Ikeuchi, Kyoto (JP); Kouji Mori, Kyoto (JP); Hiroo Iwata, Kyoto (JP)

( * ) Notice: Subject to any disclaimer, the term of this patent is extended or adjusted under 35 U.S.C. 154(b) by 147 days.

(21) Appl. No.: 10/257,407

(22) PCT Filed: Apr. 19, 2001

(86) PCT No.: PCT/JP01/03368

§ 371 (c)(1),
(2), (4) Date: Mar. 18, 2003

(87) PCT Pub. No.: WO01/80936

PCT Pub. Date: Nov. 1, 2001

(65) Prior Publication Data

US 2003/0158596 A1 Aug. 21, 2003

(51) Int. Cl.
  *A61F 2/06* (2006.01)
(52) U.S. Cl. .................................................. 623/1.15
(58) Field of Classification Search .............. 623/1.15
  See application file for complete search history.

(56) References Cited

U.S. PATENT DOCUMENTS 5,911,754 A   6/1999  Kanesaka et al.
5,922,021 A * 7/1999  Jang ......................... 623/1.15

FOREIGN PATENT DOCUMENTS

WO    96/026689    9/1996
WO    99/38457     8/1999

* cited by examiner

*Primary Examiner*—(Jackie) Tan-Uyen T. Ho
(74) *Attorney, Agent, or Firm*—Oblon, Spivak, McClelland, Maier & Neustadt, P.C.

(57) ABSTRACT

A stent (1) formed into a generally or substantially tubular body and expandable radially outward from inside of the tubular body, wherein cells (6) are connected vertically and so arranged as to surround the central axis (C1) of the stent (1) and thereby to form annular units (4), the annular units (4) are extended along the axis of the stent (1), adjacent annular units (4) are connected at least at one portion by a connecting part (5), each of the cells (6) has at least one bent portion, and the angle of the bent portion after expansion of the tubular body until the diameter becomes 2.5 mm is larger than 30°. The stent ensures a high flexibility and radial support force, enhances the blood vessel expandability, and suppresses the foreshortening phenomenon and the flare phenomenon.

48 Claims, 12 Drawing Sheets

STENT

This application claims priority of International Application No. PCT/JP01/03368 filed on Apr. 19, 2001.

TECHNICAL FIELD

The present invention relates to improvement of a stent used to improve a narrowed portion caused in a living body such as a blood vessel and the like.

TECHNICAL BACKGROUND

A stent is a tubular medical implement which is detained in the narrowed portion in question to ensure a required tubular region(space) by expanding the narrowed portion and the like when a tubular portion of a living body such as a blood vessel or other portions gets narrowed or clogged from obliteration. The stent is inserted into the body, with the diameter thereof small, and allowed to expand in the narrowed portion to make the diameter thereof large so that the tubular portion in question is expanded and kept in the expanded state.

The conventional stents, which are typically shown in FIGS. 11A, 11B and FIGS. 12A, 12B have the following problems. Incidentally, FIG. 11A and FIG. 12A are plan views showing the stents before expansion and FIG. 11B and FIG. 12B are plan views showing the stents after expansion.

In a stent 201 shown in FIG. 11A, a cell 206 constructing an annular unit 204 has a construction in which three straight line portions 207 are connected in parallel, and a curved portion 206A between each cell 206 is disposed opposite to the space 206B in the vicinity of another cell 206 constructing another annular unit 204. Because of such a construction, the stent has an appropriate radial support force (namely, as shown in FIG. 11B, a force to maintain an expansion state of the stent against the outer pressure in the direction from the blood vessel wall, when the stent is expanded and fixed on the blood vessel wall) and an excellent flexibility. On expanding or delivering of the stent, since the stent is inserted, moving along a curved line at a bent portion of the blood vessel, a portion of the cell 206 is sometimes jutted out and caught, which makes the delivery difficult (hereinafter, this is referred to as a flare phenomenon).

Meanwhile, in a stent 241 shown in FIG. 12A, cells 246 constructing an annular unit 244 have a construction in which approximately or substantially<shaped strut (a striate body) 247 is connected by a connecting part 245. Accordingly, it has the advantages that the stent is strong in radial support force, the approximately or substantially<shaped strut 247 never warps outward during expansion of the stent or when the stent passes through the bent portion of the blood vessel, and so on. However, it has a problem of shortage of flexibility. This is because there is only one bent portion in the connecting part 245 and the length of the connecting part 245 is short, as shown in FIG. 12A.

As described above, the conventional stent has a problem of not having both the flexibility and the radial support force keeping in balance.

As a result of assiduous studies to solve the above-described problem and to provide a stent having both the flexibility and the radial support force, the present inventors have reached the present invention.

DISCLOSURE OF THE INVENTION

The present invention is achieved from the point of view described above, and according to the present invention, the following invention can be provided.

[1] A stent 1 (1A, 1B) formed into a generally or substantially tubular body with annular units composed of a plurality of cells and being expandable radially outward from inside of the tubular body:

wherein the plurality of the cells 6 (6A, 6B) are connected vertically and so arranged as to surround the central axis C1 of the stent which forms the tubular body and thereby to construct annular units 4 (4A, 4B);

wherein a plurality of the annular units 4 (4A, 4B) are extended along the axis of the stent 1 (1A, 1B) to form the tubular body in such a manner that adjacent annular units 4 (4A, 4B) are connected at least at one portion by a connecting part 5 (5A, 5B); and wherein each of the cells 6 (6A, 6B) has at least one or more bent portions 12 (12A, 12B), and is formed in such a manner that the angle θ of the bent portion after expansion of the tubular body until the diameter becomes at least 2.5 mm is equal to or larger than 30°.

[2] The stent 1 (1A, 1B) according to [1], wherein the ratio of the length 6L (6AL, 6BL) to the length 5L (5AL, 5BL) of the above-described connecting part in the axial direction of the stent is formed such that when the length 6L (6AL, 6BL) of the above-described cells in the axial direction of the stent is assumed to be 100, then the length 5L (5AL, 5BL) is formed to be 50 to 100.

[3] The stent 1 (1A, 1B) according to [1] or [2], wherein the connecting part 5 (5A, 5B) is constructed of at least 2 or more of bent portions 8 and an approximately or substantially straight line portion 7 continuing to the bent portions 8, and is connected to the cells 6 (6A, 6B) constructing adjacent different annular units 4 (4A, 4B) at the ends of the cells.

[4] The stent 1 (1A) according to any one of [1] to [3], wherein the cell 6 (6A) is formed by connecting at least one or more approximately or substantially straight line portions 11 (11A) and curved line portions 13 (13A) through the bent portion 12 (12A).

[5] The stent 1B according to any one of [1] to [3], wherein the cell 6B is formed by connecting an approximately or substantially straight line portion 11B having an acute angle X with respect to the center line C2 in the axial direction of each stent 1B to an approximately or substantially straight line portion 13B disposed almost horizontally to the center line C2 in the axial direction of the stent 1B through the above-described bent portion 12B.

[6] The stent 1 (1A, 1B) according to any one of [1] to [5], wherein the connecting part 5 (5A, 5B) is constructed by connecting the bent portions 8 to the both sides of the central approximately or substantially straight line portion 7, and the end portions of the bent portion 8 are connected to the end portions of the cells 6 (6A, 6B) constructing respective adjacent different annular units 4 (4A, 4B) through the connection portions 9 (9A, 9B).

[7] The stent 1 (1A, 1B) according to any one of [1] to [6], wherein the cell 6 (6A, 6B) is formed in a vertically asymmetrical manner to the center line C2, when divided vertically with the center line C2 in the axial direction of the stent.

[8] The stent 1 (1A, 1B) according to any one of [1] to [7], wherein the connecting parts 5 (5A, 5B) are disposed at least one or more spaces apart in the radial direction of the stent 1 (1A, 1B).

Figure 1:
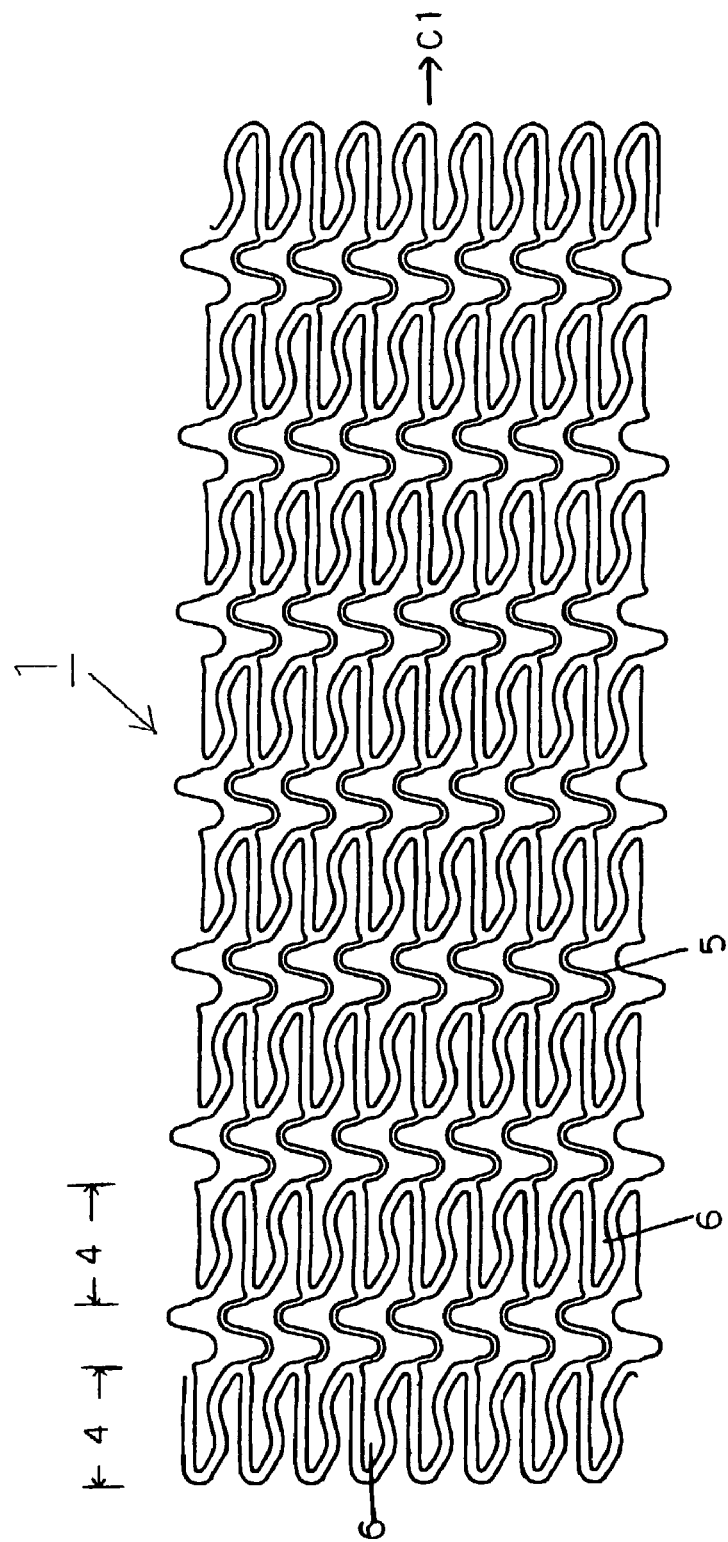
FIG. 1 is a plan view showing the stent of the present invention.

In these drawings, 1, 1A and 1B indicate the stents; 4, 4A and 4B indicate the annular units; 5, 5A and 5B indicate the connecting parts; 6, 6A and 6B indicate the cells; 7 indicates an approximately or substantially straight line portion; 8 indicates a bent portion; 9 indicates a connection portion; 11, 11A, 11B and 13B indicate approximately or substantially straight line portions; 12, 12A and 12B indicate bent portions; 13 and 13A indicate curved line portions; 14 and 14A indicate small bent portions; 15 indicates an approximately or substantially straight line portion; 17 indicates an approximately or substantially<shaped cell; 18 indicates an approximately or substantially S-shaped connecting part; and 19 indicates a unit part of the construction in the stents A, B.

Preferred Embodiments of the Invention

The present invention will be explained below in detail referring to the drawings.

Figure 3:
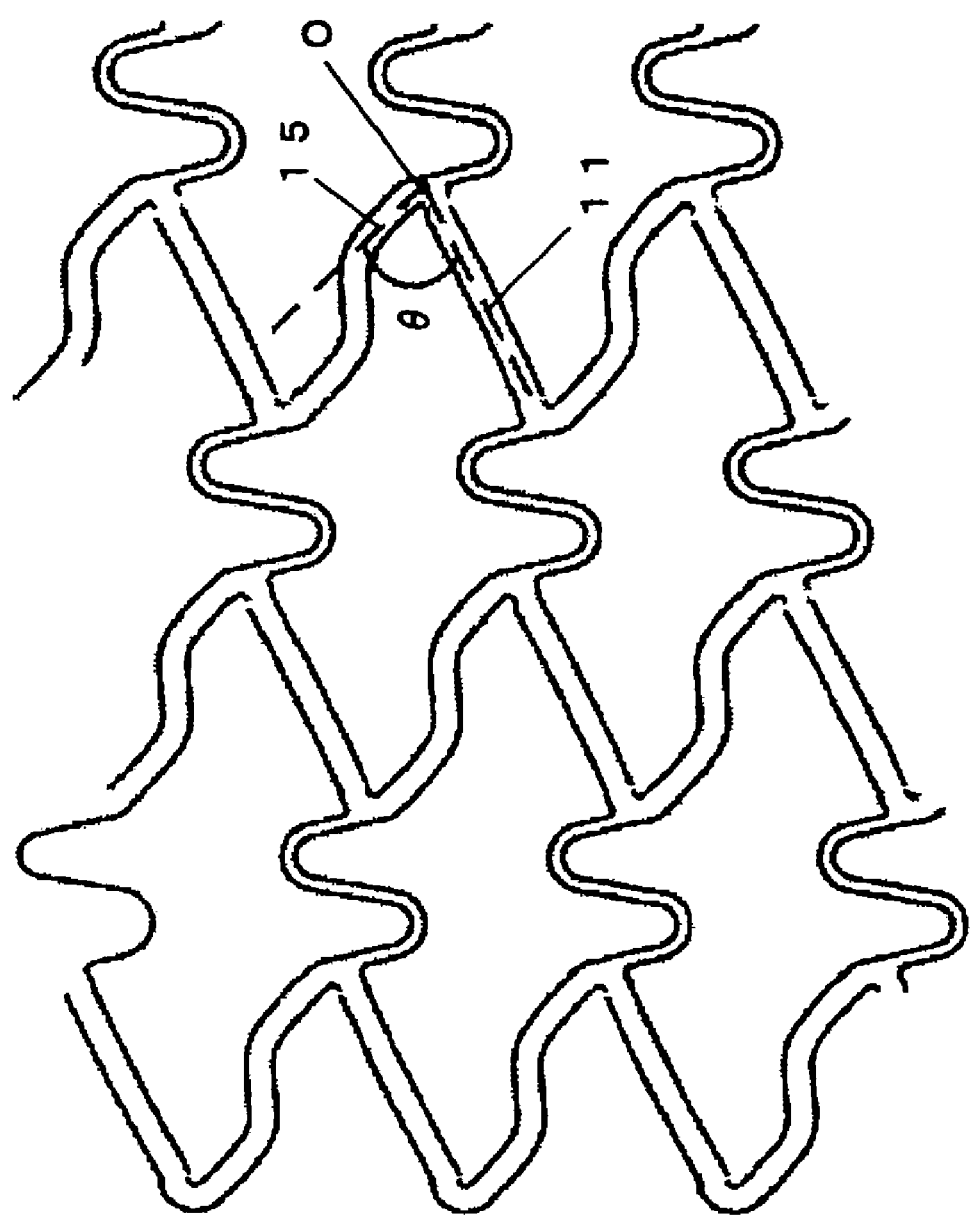
FIG. 3 is an enlarged view showing a state after expansion of the stent of the present invention.
Figure 4:
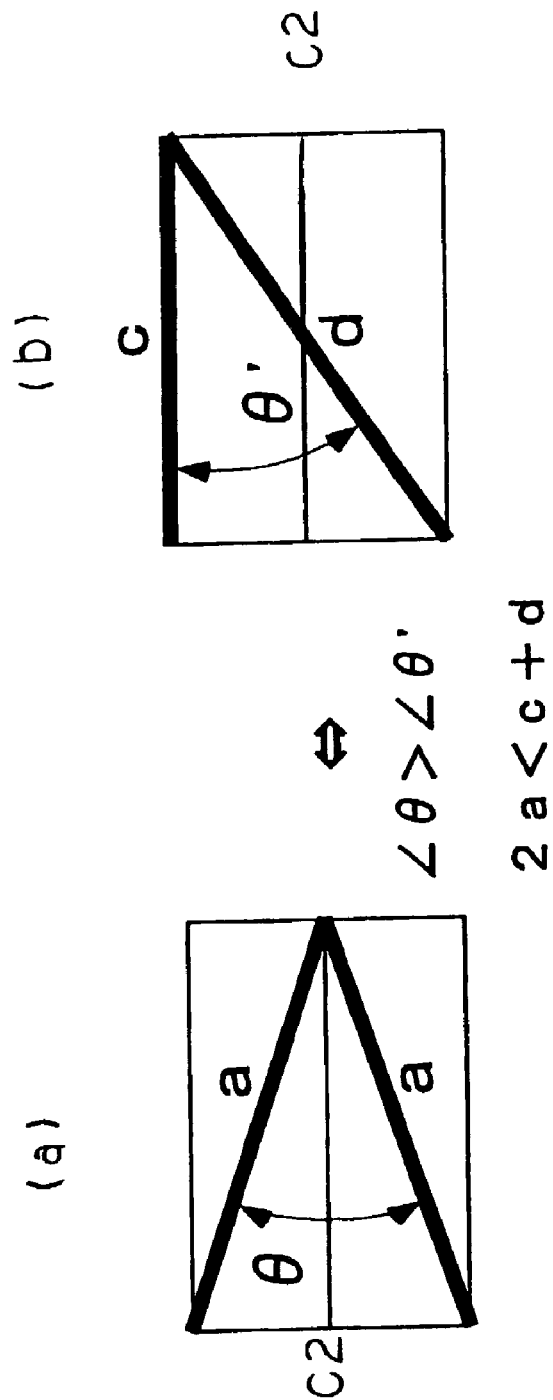
FIG. 4 is a schematic view of a strut which constructs a cell.

FIG. 1 is a plan view showing a stent of the present invention, FIG, 2 is an enlarged view of FIG. 1, FIG. 3 is an enlarged view showing a state after expansion of the stent of the present invention, and FIG. 4 is a schematic view of a strut which constructs a cell.

The stent 1 is, as shown in FIG. 1, formed into a generally or substantially tubular body from annular units 4 consisting of a plurality of cells 6, and is expandable radially outward from inside of the tubular body wherein a plurality of the cells 6 are connected vertically and so arranged to surround the central axis C1 of the stent 1 and thereby forming the annular units 4. A plurality of the annular units 4 are extended along the axis of the stent 1 which forms the tubular body in a manner that adjacent annular units 4 are connected at least at one portion by a connecting part 5.

Figure 2:
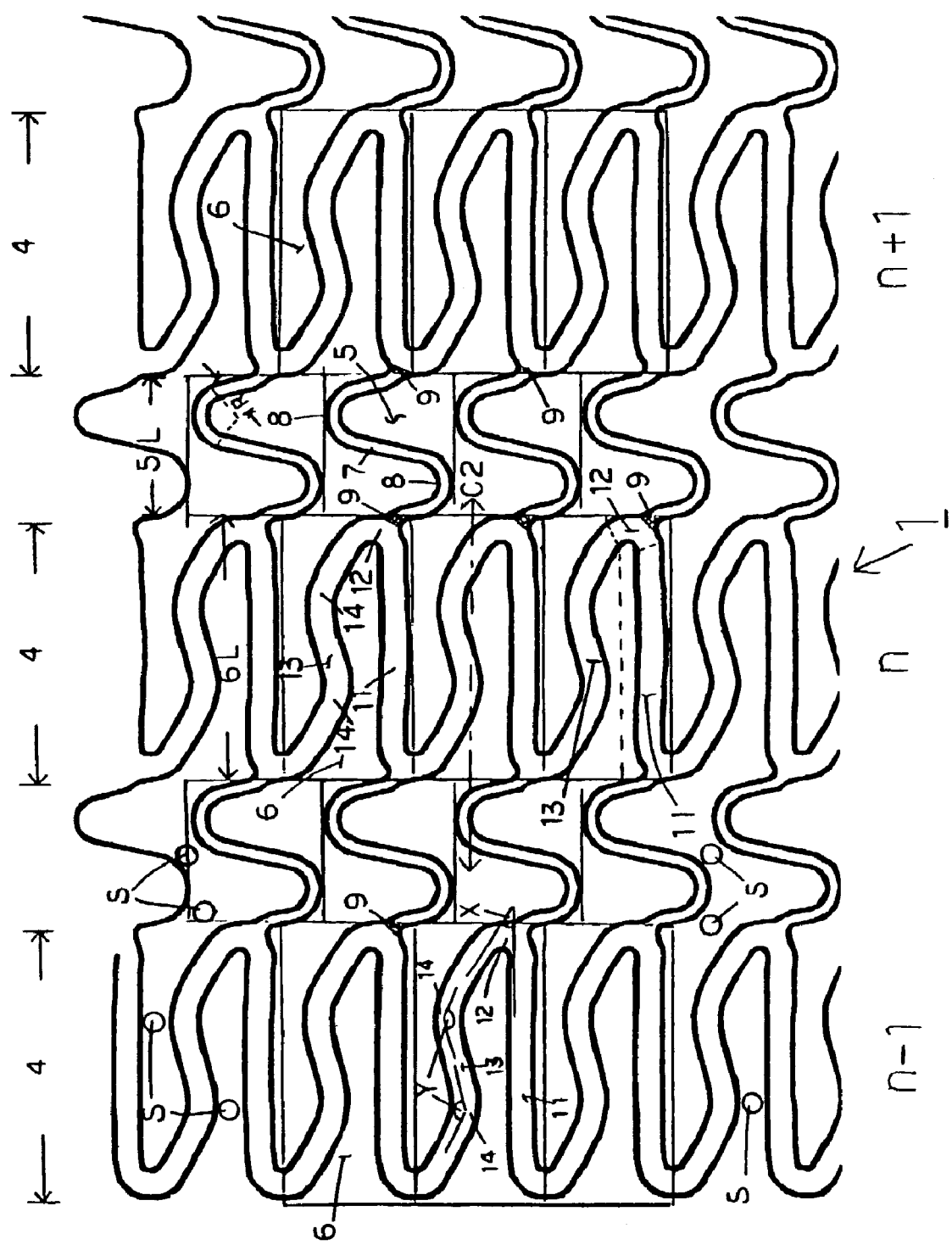
FIG. 2 is an enlarged view of FIG. 1.

In the present invention, the cell 6 means one of constitutional units of patterns consisting the surface of the stent 1 and, as shown in FIG. 2, it includes all forms having at least one or more of bent portions 12, more concretely, bent portions 12 with acute angles X, and being constructed by connecting approximately or substantially straight line portions 11 and curved line portions 13 through the bent portion 12. In addition, when each of the cells 6 is divided vertically by the center line C2 in the axial direction of the stent, the cells 6 are formed in a vertically asymmetrical manner to the center line C2 so that the angle θ of the bent portion 12 after expansion of the tubular body is 30° or more as shown in FIG. 3, when, for example, the diameter φ of the tubular body, namely of the stent, is expanded to 2.5 mm.

Incidentally, the angle θ of the bent portion 12 after expansion means, as shown in FIG. 3, an angle formed at the point 0 on the bent portion 12 between the approximately or substantially straight line portion 11 and an approximately or substantially straight line portion 15 which is near the point O side of the curved line portion 13.

The cell 6 is constructed by connecting the approximately or substantially straight line portion 11 and the curved line portion 13 through the bent portion 12 as shown in FIG. 2, and it is preferable that the curved line portion 13 is constructed by forming two or more small bent portions 14 with an obtuse angle Y.

When the approximately or substantially straight line portion 11, the bent portion 12 and the curved line portion 13 having small bent portions 14, all of which constitute the cell 6 (hereinafter also referred to as an approximately or substantially S-shaped portion) stand more perpendicularly with respect to the central axis C1 of the stent (or the tubular body) after expansion of the stent, the radial support force of the stent becomes larger. That is, as shown in FIG. 3, the closer to 180° the angle θ of the bent portion 12 after expansion reaches, the larger the radial support force of the stent becomes. Therefore, when designing the stent, it is preferable to design in such a manner that the angle θ of the bent portion 12 after expansion of the tubular body reaches at least 30° or more when the diameter φ of the tubular body becomes at least up to 2.5 mm, more preferably up to 3.0 mm.

Additionally, since these are related to the number of arrangement of the cells 6, the number of radial disposition of the cells 6 is preferably 4 or more. Furthermore, when the diameter φ of the tubular body or the stent after expansion is 3.0 mm or more, it is desirable to dispose the cells at least 6 pieces or more, preferably 6 pieces to 12 pieces.

In the axial direction of the stent, it is desirable to dispose 3 pieces or more, more preferably, 4 pieces to 8 pieces per 10 mm of the length in the axial direction of the stent, and when the diameter of the stent reaches the diameter on target for the stent expansion (spec diameter, for example, φ=3.0 mm or φ=4.0 mm), it is desirable, for example, to design the angle θ of the bent portion 12 after expansion to be at least 30° or more, preferably between 45° and 140°, more preferably between 45° and 120° as described previously.

It should be noted that, as for the diameter on target (targeted diameter), it is effective for the better radial support force of the stent to design the angle θ after expansion to be near 180°, for example, over 140°, as described above. However, it is not favorable because of the following problems such that the amount of deformation of the bent portion 12 becomes too large to maintain the strength of it in a favorable state, and the reduction in total length of the stent accompanied by the expansion (hereinafter referred to as foreshortening) becomes too large to make an easy positioning of the stent when detaining the stent.

It is preferable for the shape of the strut of the cell 6 to form asymmetrically with respect to the center line C2 of respective cells in the axial direction of the stent as shown in FIG. 4b, rather than to form symmetrically as shown in FIG. 4a. This is because that asymmetrical formation of the strut makes the relative length of the whole strut longer (for instance, when FIG. 4a is compared with FIG. 4b, it is always found to be 2 a<c+d), enhances the expandability of the stent itself, and enhances the suppression effect of the foreshortening.

The connecting part 5 between cell 6 and 6 in the stent 1 is constructed by having at least two or more of bent portions and by connecting the bent portions 8 and 8 to both sides of the central approximately or substantially straight line portion 7, and the end portions of the bent portions 8 are connected to the end portions of the cells 6 and 6 which construct respectively different (adjacent) annular units 4 and 4 through the connection portions 9 and 9, as shown in FIG. 2.

Incidentally, the connecting part 5 is connected to both sides of the cells 6 and 6 in a bilaterally asymmetrical manner, as shown in FIG. 2.

As for the length of the connecting part 5, it is preferable for the total length of the approximately or substantially straight line portion 7 and the bent portions 8 and 8 to be 1 mm or more because the flexibility of the stent is believed that the longer the total length of the stent the more the flexibility is improved. However, if it is too long, the connecting part 5 in an approximately or substantially S shape becomes proportionally large, which makes vertically adjacent connecting parts 5 interfere in each other, thereby conversely spoiling the flexibility, when the stent is mounted on a balloon catheter (the diameter of the stent may be sometimes reduced a little on the balloon catheter), or when the stent is bent along the blood vessel during passing through the bent portion of the blood vessel. Therefore, it is preferable for the total length of the connecting part to be 1 mm or more, preferably 1 mm to 2 mm. It is further desirable for R (radius) of an arc constructing the bent portion 8 to be 0.05 mm or more, preferably 0.05 mm to 0.2 mm because of the above reason.

Further, in the present invention, as shown in FIG. 2, with the ratio of the length 6L to the length 5L, it is preferable for the length 5L of the connecting part 5 in the axial direction of the stent to be 50 to 100 on the basis that the length 6L of the cells 6 in the axial direction of the stent is assumed to be 100. For convenience of design, it is more preferable to form in the length of 50 to 90. Thereby, the flare phenomenon after expansion of the stent or during delivery can be suppressed and at the same time, flexibility can be given to the stent itself.

The characteristics of the pattern of the stent 1 according to the present invention is as follows:

For example, as shown in FIG. 2, the cells 6 are disposed or placed respectively asymmetrically with respect to the center line C2 in the axial direction of the stent through the connecting part 5. However, in the axial direction of the stent, they are disposed in the same direction and at the same height. In other words, the cells 6 in the axial direction of the stent are disposed so as to align and lie on top of one another if the cells 6 are shifted in the axial direction of the stent from the nth line (column) to the (n+1)th line (column), and the cells 6 in the same line (the same annular unit) are disposed in the same direction in the radial direction of the stent so as to align and lie on top of one another if they are slid vertically from their present positions to upward or downward in the same line. Incidentally, though approximately or substantially straight line portion 11 of each cell is in substantially horizontal (substantially in parallel) to the center line C2 respectively, it may be inclined at some angles in a range not to be less than 30° of the angle θ of the bent portion 12 after expansion.

Further, though the connecting parts 5 are also disposed asymmetrically in the axial direction of the stent through the cell 6, they are disposed facing in the same direction in the axial direction of the stent and at the same height. In other words, the connecting parts 5 in the axial direction of the stent are seen to be disposed so as to align and lie on top of one another if the connecting parts 5 are shifted in the axial direction of the stent from the nth line to the (n+1)th line, and the connecting parts in the same line are seen to be disposed in the same direction in the radial direction of the stent so as to align and lie on top of one another if they are slid vertically from their present positions to upward or downward of the same line.

In the stent of the present invention, the width of the strut constructing the cell 6 is preferably wider than the width of the strut constructing the connecting part 5, and the heights of the cell 6 and the connecting part 5 in the axial direction of the stent are preferably disposed in such a manner that both are shifted to each other so as to be at a different height from each other, not to be at the same height.

Figure 5:
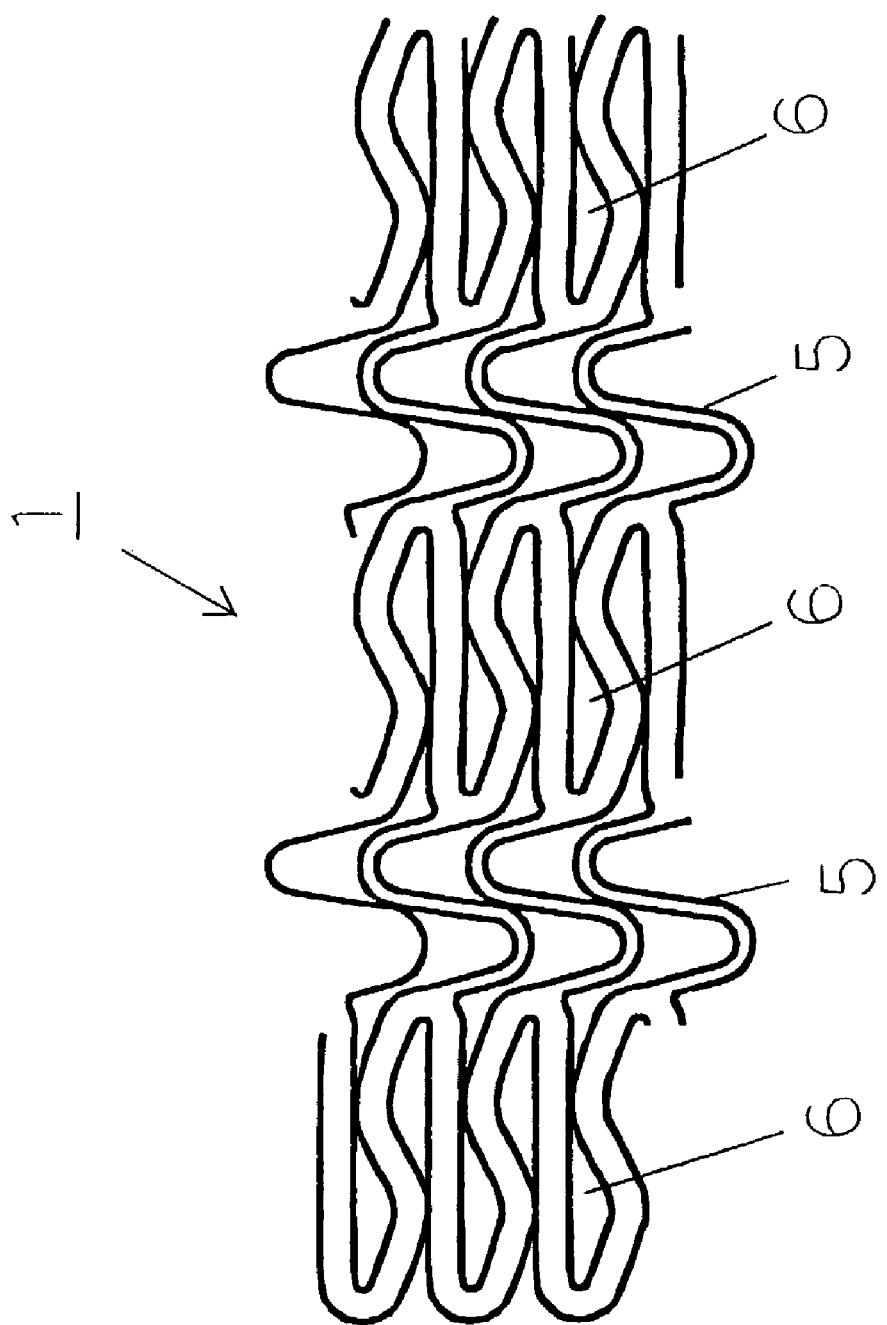
FIG. 5 is an enlarged view when the diameter of the stent is reduced on delivering to a flood vessel.

As described above, in the stent 1 of the present invention, by specifying the angle θ of the bent portion 12 after expansion, the ratio of the length 6L in the axial direction of the stent of the cell 6 to the length 5L in the axial direction of the stent of the connecting part, the shape and size of the connecting part 5 and the cell 6, the disposition (pattern) in the radial direction and the axial direction of the stent of the connecting part 5 and the cell 6 as above, the cells 6 and the connecting parts 5 do not align and do not lie respectively on top of one another three-dimensionally in the radial direction of the stent when the diameter of the stent 1 is reduced during delivering to the blood vessel as shown in FIG. 5. That is, when the diameter of the stent 1 is reduced as shown in FIG. 5, they are formed to fit in the space S in the radial direction of the stent existing between each of the cells 6 and the connecting parts 5 as shown in FIG. 2.

Figure 6:
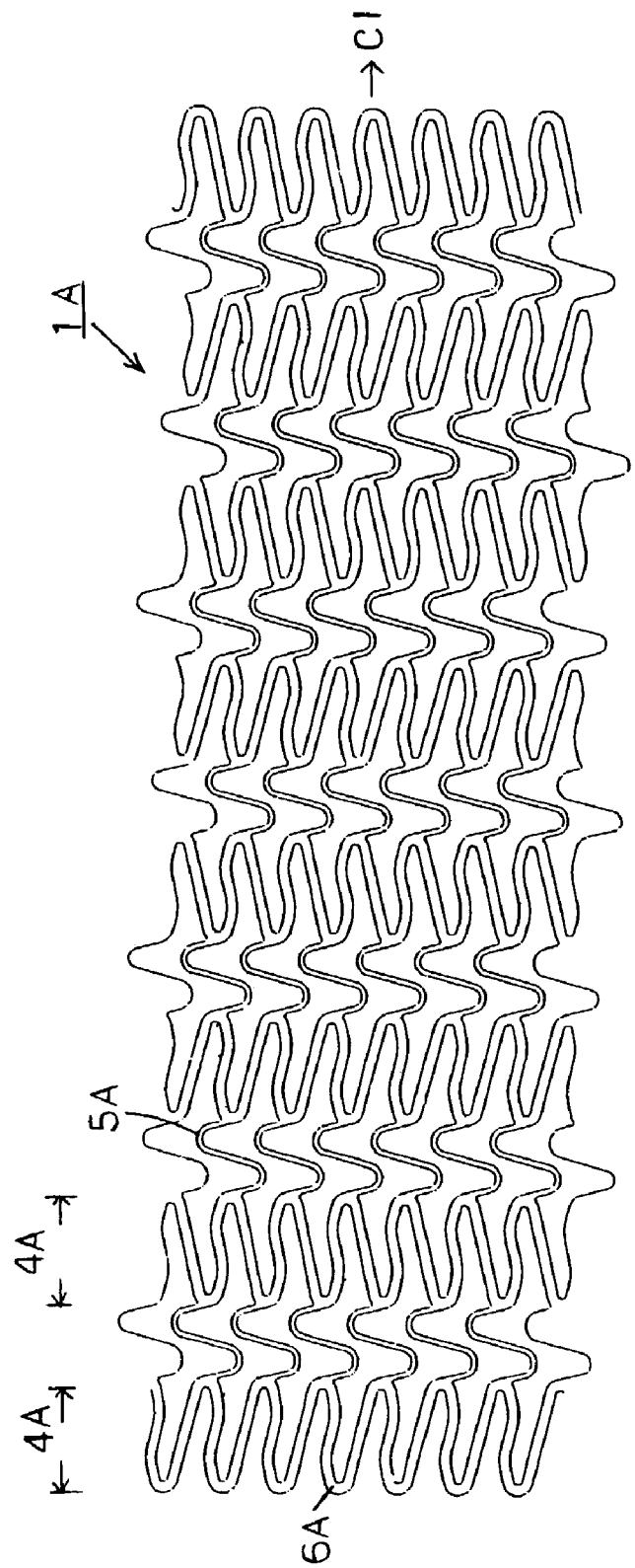
FIG. 6 is a plan view showing an example of another embodiment of the stent according to the present invention.
Figure 7:
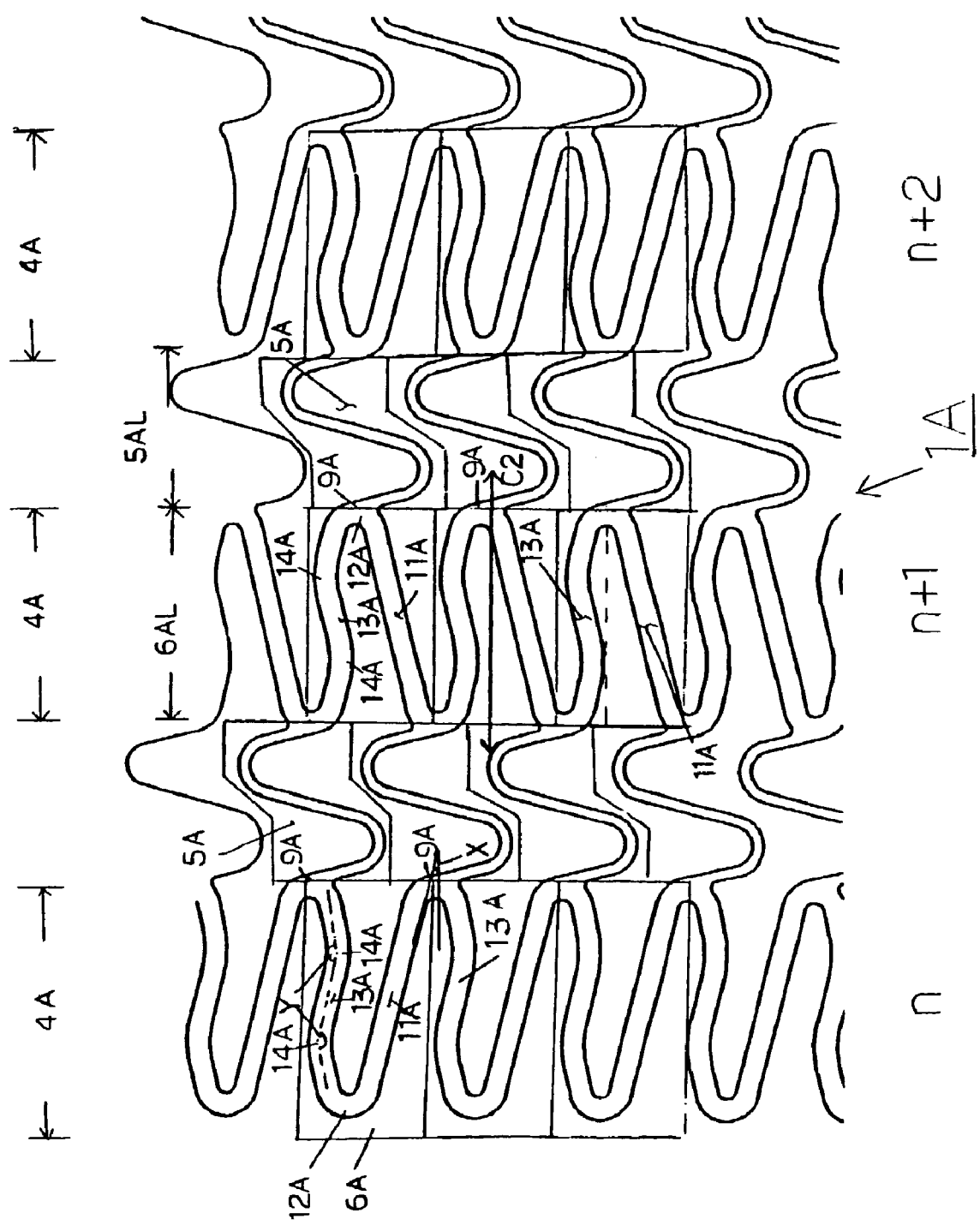
FIG. 7 is a partially enlarged plan view of FIG. 6.
Figure 8:
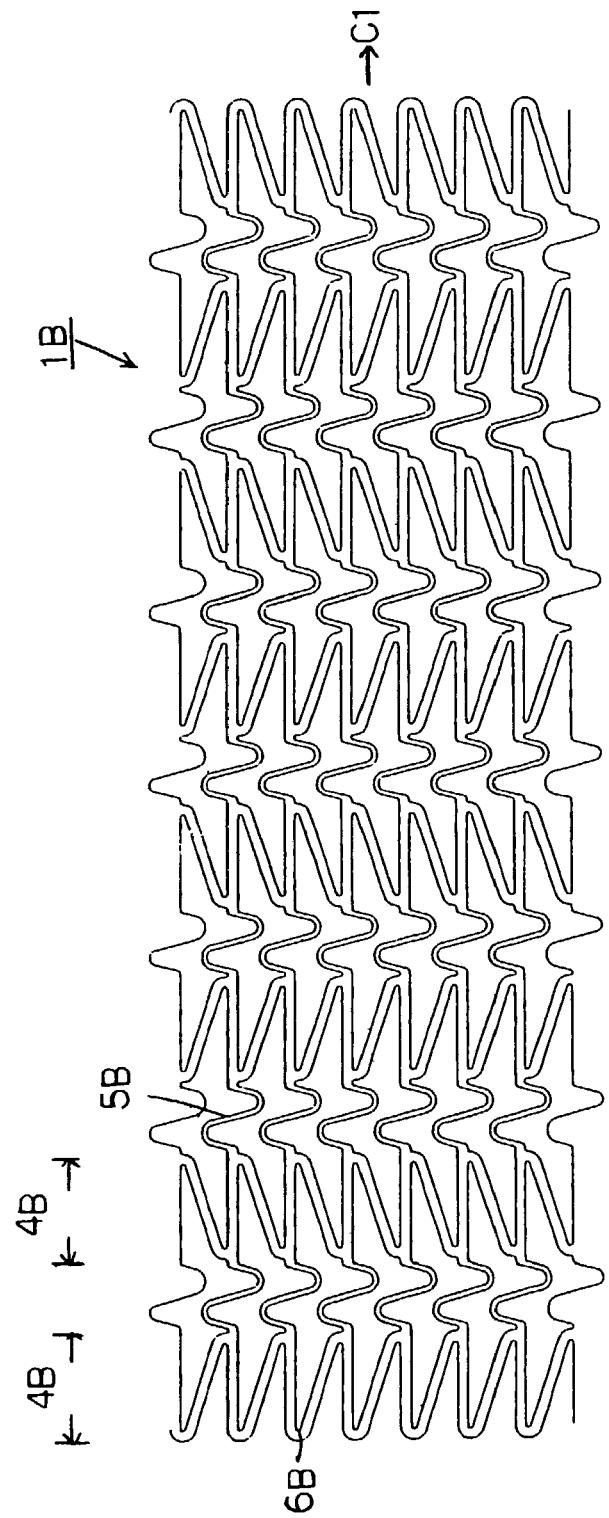
FIG. 8 is a plan view showing an example of yet another embodiment of the stent according to the present invention.
Figure 9:
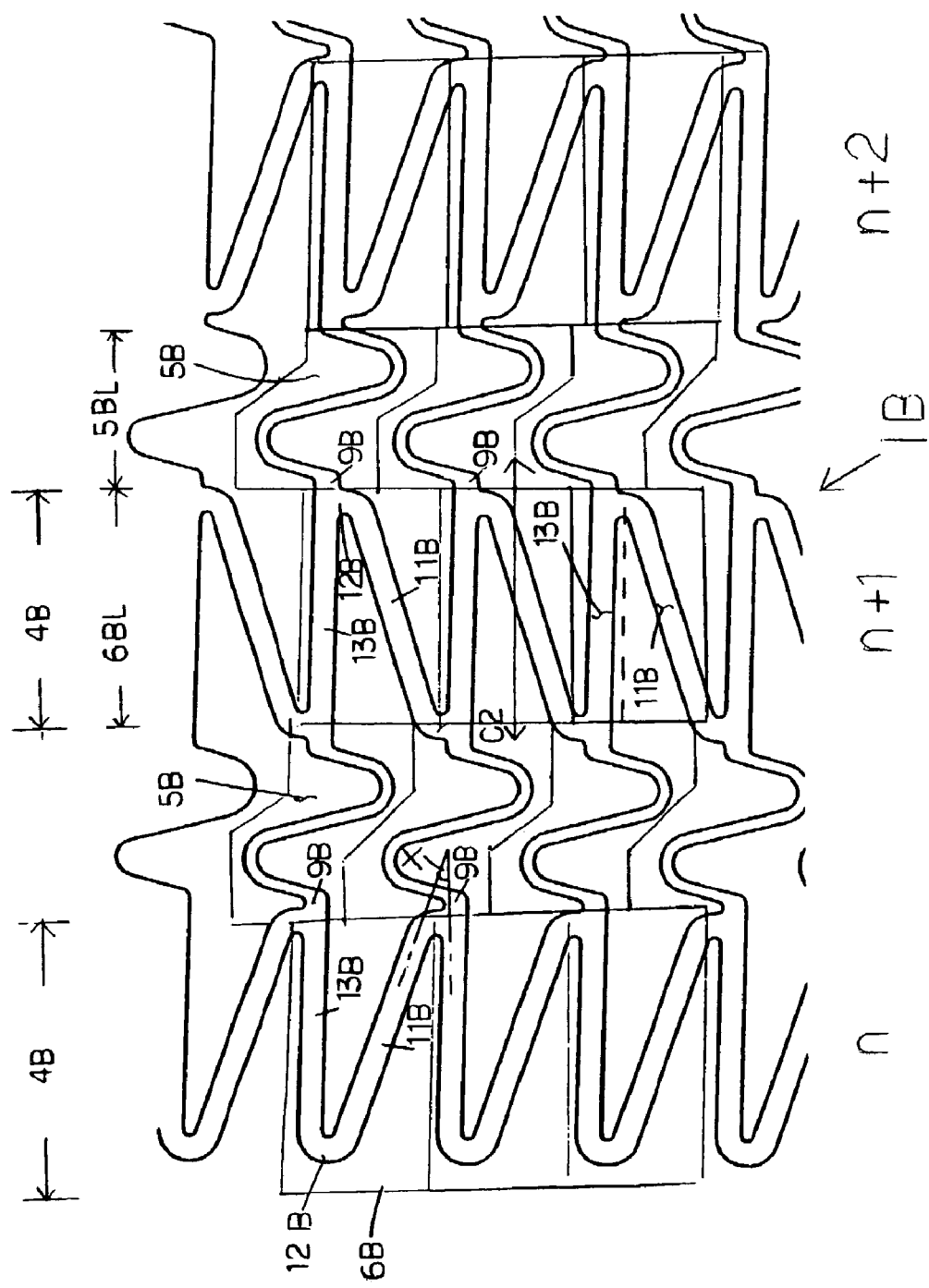
FIG. 9 is a partially enlarged plan view of FIG. 8.

FIG. 6 and FIG. 8 are plan views showing examples of other embodiments of the present invention and FIG. 7 and FIG. 9 are partially enlarged plan views of FIG. 6 and FIG. 8 respectively.

The stent 1A shown in FIG. 6 and FIG. 7 is basically the same excepting only the following point when compared with the stent 1 shown in FIG. 1. That is, (a) each of the cells 6A is constructed by connecting approximately or substantially straight line portion 11A having an acute angle X with respect to respective center line C2 in the axial direction of the stent 1A to the curved line portion 13A through the bent portion 12A (while the stent 1 is constructed by connecting approximately or substantially straight line portion 11 disposed almost horizontally (substantially in parallel) with respect to respective center line C2 in the axial direction of the stent 1 to the curved line portion 13 through the bent portion 12), (b) the cells 6A are disposed in a bilaterally symmetrical manner in the axial direction of the stent 1A through the connecting part 5A, (c) the cells 6A in the axial direction of the stent 1A are disposed to align and lie on top of one another when seen from the cells in the nth line to the cells in the (n+2)th line, on every other line in the axial direction of the stent 1A. Since respective other construction members and the definitions thereof are substantially the same as those in the stent 1, the detailed explanation thereof will be omitted here.

Furthermore, the stent 1B shown in FIG. 8 and FIG. 9 is different from the stents 1 and 1A shown in FIG. 1, FIG. 6 and FIG. 7 only in the point that (a) each of the cells 6B is constructed by connecting an approximately or substantially straight line portion 11B having an acute angle X with respect to respective center lines C2 in the axial direction of the stent 1B to an approximately or substantially straight line portion 13B disposed almost horizontally (substantially in parallel) with the center line C2 in the axial direction of the stent 1 through the bent portion 12B (while in the stent 1, and stent 1A, each of the cells 6 and 6A is constructed by connecting the approximately or substantially straight line portion 11, 11A to the curved line portion 13, 13A through the bent portion 12). Though the following points of (b) respective cells 6B are disposed in a bilaterally symmetrical manner in the axial direction of the stent 1B through the connecting part 5B, and (c) the cells 6B in the axial direction of the stent 1B are disposed to align and lie on top of one another when seen in the axial direction of the stent 1B from the cells in the nth line to those in the (n+2)th line, on every other line in the axial direction of the stent 1B are different from the stent 1, the stent 1B is substantially the same with the points of (b) and (c) as those in the stent 1A. Since respective other construction members and the definitions thereof are substantially the same as those in the stent 1 and the stent 1A, the detailed explanation thereof will be omitted here.

In the stents 1, 1A and 1B shown in the above-described FIG. 1, FIG. 6 and FIG. 8 of the present invention, though the connecting parts 5, 5A and 5B of the cells 6, 6A and 6B constructing respective annular units 4, 4A and 4B are disposed continuously without space in the radial direction of the stents 1, 1A and 1B, they may be disposed with at least one or more spaces in the radial direction. Thus, by disposing the connecting parts suitably with one space apart or one or two spaces apart, the whole stents 1, 1A, 1B become more flexible so that the deliverability to branched blood vessels is expected to improve.

As a material constructing the stents 1, 1A, 1B of the present invention, well-known materials itself can be used without any limitation and a metal pipe made of, for example, stainless steel such as SUS 316L and the like, a shape memory alloy such as Ti—Ni alloy, Cu—Al—Mn alloy and so on, Cu—Zn alloy, Ni—Al alloy, titan, titan alloy, tantalum, tantalum alloy, platinum, platinum alloy, tungsten and tungsten alloy is used to form the stent by a laser processing method or other processing method.

On the surface of the stent formed with these metals, a polymeric material having compatibility with a living body such as polyurethane, polyvinyl pyrrolidine, or polyvinyl alcohol, or a material in which the above polymeric material is fixed with a physiologically active substance such as heparin, urokinase and the like by chemical bonding, and a material in which the above polymeric material is mixed with an antithrombosis medicine such as argatroban, cilostazol, sarpogrelate HCl, and so on may be applied as a coating.

EXAMPLE 1

Figure 10:
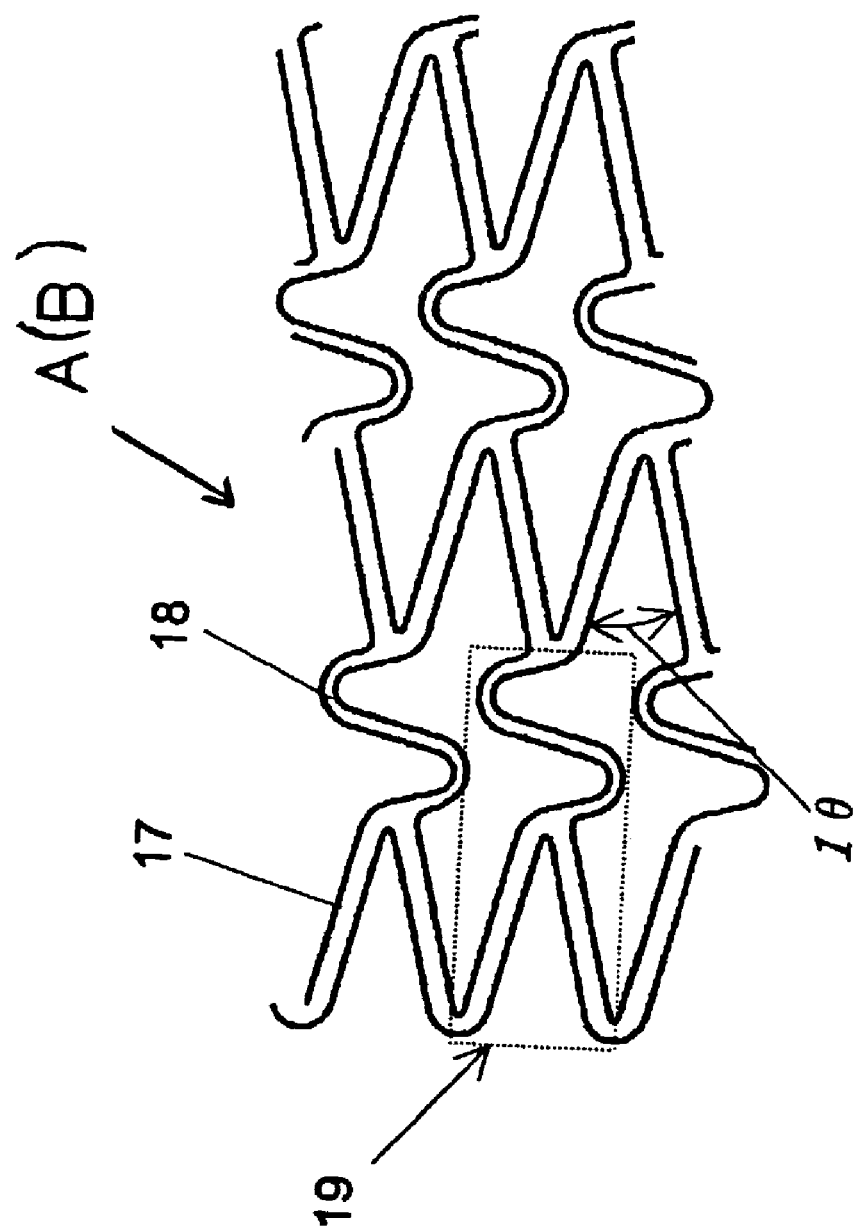
FIG. 10 is an enlarged view of a reference example of the stent according to the present invention.

In the stent A (B) constructed by unit parts 19 of the construction consisting of approximately or substantially<shaped cells 17 and approximately or substantially S-shaped connecting parts 18, as shown in FIG. 10, in order to evaluate difference in radial support force due to the difference of the angle after expansion, the stent A (the number of arrangement: 8) and the stent B (the number of arrangement: 6) which are different in the number of arrangement of the unit parts 19 of the construction in the circumferential direction, are prepared as below, and respective radial support forces are evaluated and compared.

stent A:

| the number of the unit parts 19 to be arranged | 8 |
| strut width of the cell 17 | 0.12 mm |
| 1 θ angle after expansion by 3 mm | 60° | stent B:

| the number of the unit parts 19 to be arranged | 6 |
| strut width of the cell 17 | 0.12 mm |
| 1 θ angle after expansion by 3 mm | 81° |

The evaluation is carried out by expanding respective stents in a silicone tube disposed in a chamber by 3 mm of the diameter φ. After detaining them, change in the outer diameter of the stents while applying pressure in the chamber with air is measured to evaluate. The measurement result is shown in Table 1.

TABLE 1

(measurement result of the radial support force)

| | stent A | stent B |
|---|---|---|
| amount of change in the outer diameter when applying pressure of 0.02 MPa | −0.07 mm | −0.04 mm |

As clearly shown in Table 1, while the amount of change in the outer diameter is −0.04 mm (which means the outer diameter is shortened by 0.04 mm) in the stent B having a larger angle (1θ) after expansion, the amount of change in the outer diameter is −0.07 mm (which means the outer diameter is shortened by 0.07 mm) in the stent A. Thus, it was confirmed that the stent B is smaller in the amount of change in the outer diameter and larger in the radial support force.

EXAMPLE 2

Figure 11:
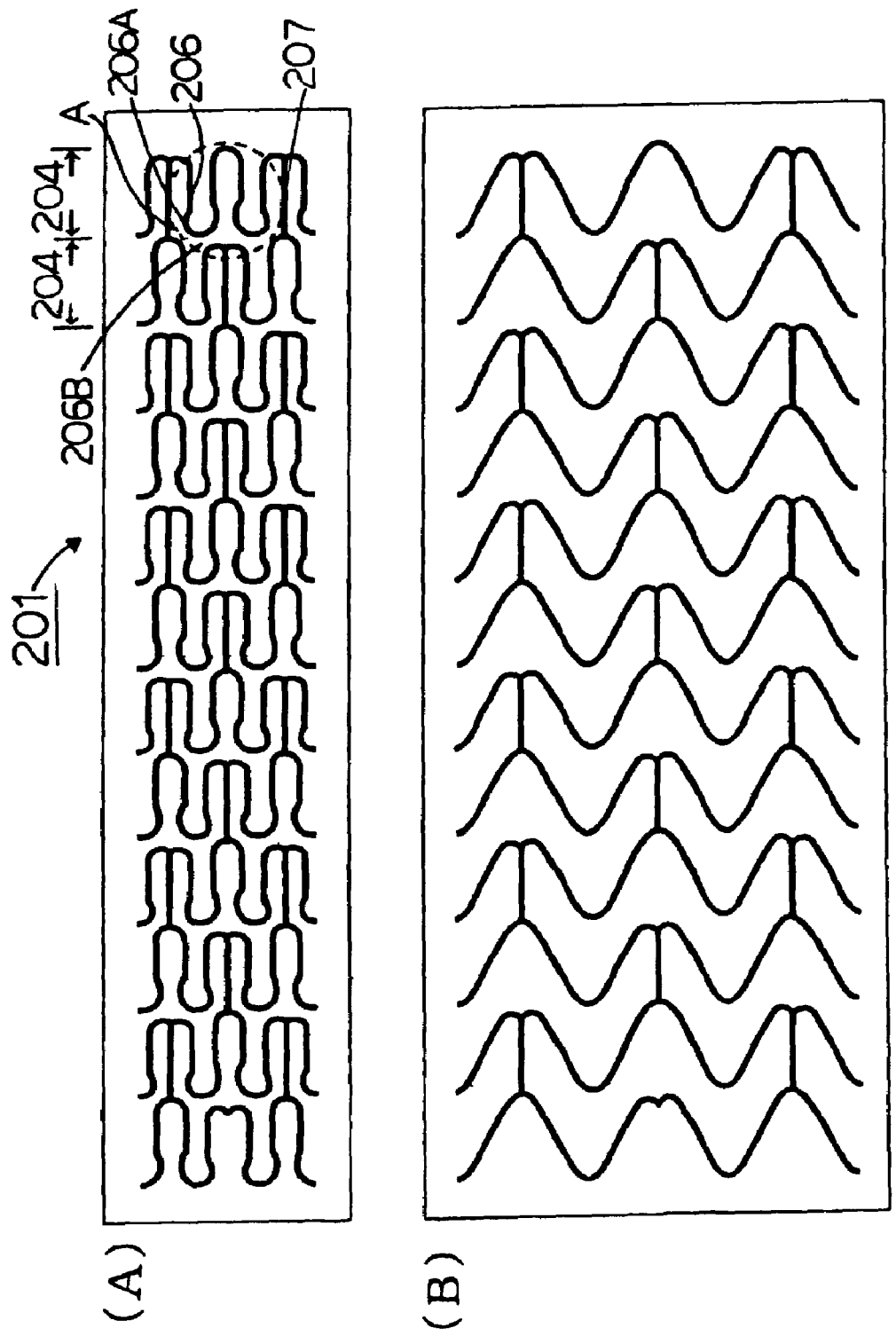
FIGS. 11A, 11B and FIGS. 12A, 12B are plan views of conventional stents respectively.
Figure 12:
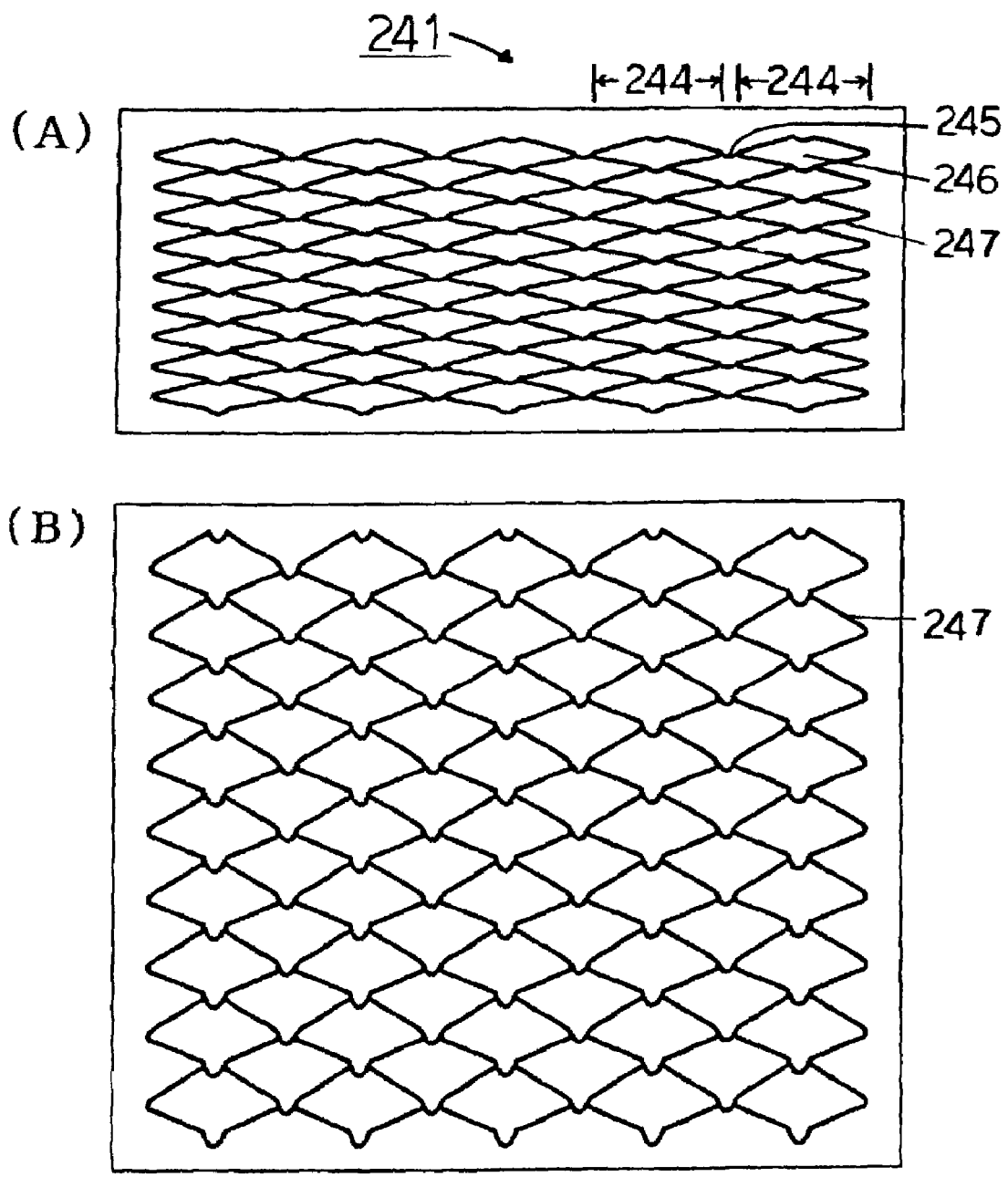

The stent 1 shown in FIG. 1 was prepared, and the radial support force was compared with conventional stents 201 (FIG. 11) and 241 (FIG. 12) and the flexibility was compared with the stent 201 to evaluate. The evaluation of the radial support force was carried out in the same manner as in the example 1, and the flexibility was evaluated by the 4 point bending test. The measurement result of the radial support force is shown in Table 2 and the measurement result of the flexibility is shown in Table 3.

TABLE 2

(measurement result of the radial support force)

| | stent 1 | stent 201 | stent 241 |
|---|---|---|---|
| amount of change in the outer diameter when applying pressure of 0.02 MPa | −0.026 mm | −0.05 mm | −0.030 mm |

TABLE 3

(measurement result of the flexibility)

| | stent 1 | stent 201 |
|---|---|---|
| flexural strength | 11.7N · mm | 17.1N · mm |

As clearly shown in Table 2, it is recognized that the amount of change in the outer diameter of the stent 1 of the present invention is smaller than those of both the stent 201 and the stent 241, and, as is clear from the result in Table 3, the flexural strength is smaller than that of the stent 201. As described above, the stent 1 of the present invention is recognized to be a stent having both a high radial support force and high flexibility.

EXAMPLE 3

The radial support force and the flexibility of the stent 1A shown in FIG. 6 (FIG. 7) and the stent 1B shown in FIG. 8

(FIG. 9) were measured and evaluated in the same manner as in Example 1 and Example 2. The measurement result of the radial support force is shown in Table 4 and the measurement result of the flexibility is shown in Table 5. As is clear from Tables, it is recognized that substantially the same results as in the stent 1 are obtained also as for the stent 1A and the stent 1B.

TABLE 4

(measurement result of the radial support force)

| | stent 1A | stent 1B | stent 201 | stent 241 |
|---|---|---|---|---|
| amount of change in the outer diameter when applying pressure of 0.02 MPa | −0.033 mm | −0.031 mm | −0.05 mm | −0.030 mm |

TABLE 5

(measurement result of the flexibility)

| | stent 1A | stent 1B | stent 201 |
|---|---|---|---|
| flexural strength | 13.7N · mm | 14.3N · mm | 17.1N · mm |

EXAMPLE 4

As for the stents 1, 1A, 1B in the present invention, the foreshortening values when the diameter φ of the stents were expanded to 3.0 mm were measured. The measurement was carried out in such a manner that each stent length (referred to as L1) before expansion and the corresponding stent length (referred to as L2) after expansion to 3.0 mmφ were measured and the reduction ratios of the total length were calculated with the following formula to have the foreshortening value. Foreshortening value=((L1−L2)/L1)×100

As comparison examples, the same measurements were made for the stent 201 and the stent 241. The result is shown in Table 6.

TABLE 6

| | stent 1 | stent 1A | stent 1B | stent 201 | stent 241 |
|---|---|---|---|---|---|
| foreshortening value | 1.5% | 1.5% | 3% | 5.6% | 5.6% |

As is clear from Table 6, the foreshortening values of all stents 1, 1A and 1B of the present invention are recognized to be far smaller than those of the conventional stents 201 and 241.

INDUSTRIAL UTILITY

The stent of the present invention can ensure sufficiently both of high flexibility and a high radial support force and at the same time enhance the expandability of the blood vessel and suppress the foreshortening and the flare phenomenon, so that it can be preferably used as a stent to expand a narrowed portion of the blood vessel to ensure a necessary and important tubular region.

What is claimed is:

1. A stent formed into a generally or substantially tubular body comprising:
   annular units composed of a plurality of cells, said annular units radially expandable outward from inside of the tubular body,
   wherein the plurality of the cells of each annular unit are connected vertically and arranged surrounding a central axis of the stent;
   wherein said annular units are disposed along an axial direction of said stent, and adjacent annular units are connected at least at one portion by a connecting part;
   said connecting part being a generally S-shaped connecting part, said S-shaped connecting part including two or more arcs and a substantially straight line portion between two arcs, each free end of the arcs extending substantially upward or downward as high as about a middle of said straight line portion thereby forming a full fledged S-shaped connecting part, and ends of said connecting part are respectively connected to a left portion and a right portion of cells forming adjacent annular units respectively;
   each cell being composed of two struts, a first substantially straight strut being disposed in the axial direction as a base strut (BS-strut), and a second curved strut disposed at an acute angle X with respect to the axial direction of the stent as a bending strut (BN-strut), and said acute angle X being substantially maintained between a major or majority part of said first straight strut (BS-strut) and a major or majority part of the second curved strut (BN-strut) thereby the majority part of the base strut (BS-strut) and the majority part of the bending strut (BN-strut) are substantially not in parallel with each other,
   wherein a substantially straight line portion forming a part of said second curved strut (BN-strut) is connected to the first substantially straight strut (BS-strut) via a bent portion,
   thereby the stent is configured to be compressed such that said first straight strut composing the base strut remains in the axial direction, and said second curved strut composing the bending strut bends toward the base strut, and
   said stent being expandable to at least a diameter of 2.5 mm when an angle formed between said first strut and said substantially straight line portion of the second strut is 30°–140°.

2. The stent according to claim 1, wherein a ratio of a length of said cell in the axial direction of the stent to a length of said connecting part in the axial direction of the stent is such that when the length of said cell in the axial direction of the stent is 100, the length of said connecting part in the axial direction of the stent is 50 to 100.

3. The stent according to claim 2, wherein said cells are all equal in size.

4. The stent according to claim 2, wherein said cells are bilaterally symmetric in the axial direction of the stent through the connecting parts.

5. The stent according to claim 4, wherein said cells are all equal in size.

6. The stent according to claim 2, wherein said connecting parts are configured to be disposed at intervals of at least one connecting part, putting at least one or more spaces therebetween without disposing the connecting parts continuously and spacelessly in a radial direction of the stent.

7. The stent according to claim 6, wherein said cells are bilaterally symmetric in the axial direction of the stent through the connecting parts.

8. The stent according to claim 7, wherein said cells are all equal in size.

9. The stent according to claim 6, wherein said cells are all equal in size.

10. The stent according to claim 1, wherein said connecting parts are configured to be disposed at intervals of at least one connecting part, putting at least one or more spaces therebetween without disposing the connecting parts continuously and spacelessly in a radial direction of the stent.

11. The stent according to claim 10, wherein said cells are bilaterally symmetric in the axial direction of the stent through the connecting parts.

12. The stent according to claim 10, wherein said cells are all equal in size.

13. The stent according to claim 11, wherein said cells are all equal in size.

14. The stent according to claim 1, wherein said cells are bilaterally symmetric in the axial direction of the stent through the connecting parts.

15. The stent according to claim 14, wherein said cells are all equal in size.

16. The stent according to claim 1, wherein said cells are all equal in size.

17. A stent formed into a generally or substantially tubular body comprising:
- annular units composed of a plurality of cells, said annular units radially expandable outward from inside of the tubular body,
- wherein the plurality of the cells of each annular unit are connected vertically and arranged surrounding a central axis of the stent;
- wherein said annular units are disposed along an axial direction of said stent, and adjacent annular units are connected at least at one portion by a connecting part;
- said connecting part being a generally S-shaped connecting part, said S-shaped connecting part including two or more arcs and a substantially straight line portion between two arcs, each free end of the arcs extending substantially upward or downward as high as about a middle of said straight line portion thereby forming a full fledged S-shaped connecting part, and ends of said connecting part are respectively connected to a left portion and a right portion of cells forming adjacent annular units respectively;
- each cell being composed of two struts, a first curved strut being disposed in the axial direction as a base strut (BS-strut), and a second substantially straight strut disposed at an acute angle X with respect to the axial direction of the stent as a bending strut (BN-strut), and said acute angle X being substantially maintained between a major or majority part of said first curved strut (BS-strut) and a major or majority part of the second substantially straight strut (BN-strut) thereby the majority part of the base strut (BS-strut) and the majority part of the bending strut (BN-strut) are substantially not in parallel with each other,
- wherein a substantially straight line portion forming a part of said first curved strut (BS-strut) is connected to the second substantially straight strut (BN-strut) via a bent portion,
- thereby the stent is configured to be compressed such that said first curved strut composing the base strut remains in the axial direction, and said second straight strut composing the bending strut bends toward the base strut, and
- said stent being expandable to at least a diameter of 2.5 mm when an angle formed between said substantially straight line portion of said first curved strut and the second substantially straight strut is 30°–140°.

18. The stent according to claim 17, wherein a ratio of a length of said cell in the axial direction of the stent to a length of said connecting part in the axial direction of the stent is such that when the length of said cell in the axial direction of the stent is 100, then the length of said connecting part in the axial direction of the stent is 50 to 100.

19. The stent according to claim 18, wherein said cells are all equal in size.

20. The stent according to claim 18, wherein said cells are bilaterally symmetric in the axial direction of the stent through the connecting parts.

21. The stent according to claim 20, wherein said cells are all equal in size.

22. The stent according to claim 18, wherein said connecting parts are configured to be disposed at intervals of at least one connecting part, putting at least one or more spaces therebetween without disposing the connecting parts continuously and spacelessly in a radial direction of the stent.

23. The stent according to claim 22, wherein said cells are bilaterally symmetric in the axial direction of the stent through the connecting parts.

24. The stent according to claim 23, wherein said cells are all equal in size.

25. The stent according to claim 22, wherein said cells are all equal in size.

26. The stent according to claim 17, wherein said cells are bilaterally symmetric in the axial direction of the stent through the connecting parts.

27. The stent according to claim 26, wherein said cells are all equal in size.

28. The stent according to claim 17, wherein said cells are all equal in size.

29. The stent according to claim 17, wherein said connecting parts are configured to be disposed at intervals of at least one connecting part, putting at least one or more spaces therebetween without disposing the connecting parts continuously and spacelessly in a radial direction of the stent.

30. The stent according to claim 29, wherein said cells are all equal in size.

31. The stent according to claim 29, wherein said cells are bilaterally symmetric in the axial direction of the stent through the connecting parts.

32. The stent according to claim 31, wherein said cells are all equal in size.

33. A stent formed into a generally or substantially tubular body comprising:
- annular units composed of a plurality of cells, said annular units radially expandable outward from inside of the tubular body,
- wherein the plurality of the cells of each annular unit are connected vertically and arranged surrounding a central axis of the stent;
- wherein said annular units are disposed along an axial direction of said stent, and adjacent annular units are connected at least at one portion by a connecting part;
- said connecting part being a generally S-shaped connecting part, said S-shaped connecting part including two or more arcs and a substantially straight line portion between two arcs, each free end of the arcs extending substantially upward or downward as high as about a middle of said straight line portion thereby forming a full fledged S-shaped connecting part, and ends of said connecting part are respectively connected to a left portion and a right portion of cells forming adjacent annular units respectively;

each cell being composed of two struts, wherein one strut of the two being substantially straight strut and an other being a curved strut, and wherein one strut of the two being disposed in the axial direction as a base strut (BS-strut), and the other strut disposed at an acute angle X with respect to the axial direction of the stent as a bending strut (BN-strut), and said acute angle X being substantially maintained between a major or majority part of said first base strut and a major or majority part of second bending strut, thereby the majority part of the base strut (BS-strut) and the majority part of the bending strut (BN-strut) are substantially not in parallel with each other, wherein said two struts are connected via a bent portion, the stent is configured to be compressed such that said first strut composing the base strut remains in the axial direction, and said second strut composing the bending strut bends toward the base strut, and said stent being expandable to at least a diameter of 2.5 mm when an angle formed between said two struts is 30°–140°.

34. The stent according to claim 33, wherein said cells are all equal in size.

35. The stent according to claim 33, wherein a ratio of a length of said cell in the axial direction of the stent to a length of said connecting part in the axial direction of the stent is such that when the length of said cell in the axial direction of the stent is 100, the length of said connecting part in the axial direction of the stent is 50 to 100.

36. The stent according to claim 35, wherein said cells are all equal in size.

37. The stent according to claim 35, wherein said cells are bilaterally symmetric in the axial direction of the stent through the connecting parts.

38. The stent according to claim 37, wherein said cells are all equal in size.

39. The stent according to claim 35, wherein said connecting parts are configured to be disposed at intervals of at least one connecting part, puffing at least one or more spaces therebetween without disposing the connecting parts continuously and spacelessly in a radial direction of the stent.

40. The stent according to claim 39, wherein said cells are all equal in size.

41. The stent according to claim 39, wherein said cells are bilaterally symmetric in the axial direction of the stent through the connecting parts.

42. The stent according to claim 41, wherein said cells are all equal in size.

43. The stent according to claim 33, wherein said cells are bilaterally symmetric in the axial direction of the stent through the connecting parts.

44. The stent according to claim 43, wherein said cells are all equal in size.

45. The stent according to claim 33, wherein said connecting parts are configured to be disposed at intervals of at least one connecting part, putting at least one or more spaces therebetween without disposing the connecting parts continuously and spacelessly in a radial direction of the stent.

46. The stent according to claim 45, wherein said cells are all equal in size.

47. The stent according to claim 45, wherein said cells are bilaterally symmetric in the axial direction of the stent through the connecting parts.

48. The stent according to claim 47, wherein said cells are all equal in size.

* * * * *

UNITED STATES PATENT AND TRADEMARK OFFICE
CERTIFICATE OF CORRECTION

| | | |
|---|---|---|
| PATENT NO. | : 7,179,285 B2 | Page 1 of 1 |
| APPLICATION NO. | : 10/257407 | |
| DATED | : February 20, 2007 | |
| INVENTOR(S) | : Ikeuchi et al. | |

It is certified that error appears in the above-identified patent and that said Letters Patent is hereby corrected as shown below:

On the title page, Item (30), the Foreign Priority Data has been omitted. Item (30) should read:

-- [30] Foreign Application Priority Data
Apr. 20, 2000 (JP) .......................... 2000-118939
Aug. 04, 2000 (JP) .......................... 2000-236340--

Signed and Sealed this

Eighth Day of May, 2007

JON W. DUDAS
*Director of the United States Patent and Trademark Office*